(12) United States Patent
Kwon et al.

(10) Patent No.: US 10,765,642 B2
(45) Date of Patent: Sep. 8, 2020

(54) COMPOSITION FOR PREVENTING OR TREATING MUSCLE WEAKNESS-RELATED DISEASES COMPRISING SOBREROL

(71) Applicants: KOREA RESEARCH INSTITUTE OF BIOSCIENCE AND BIOTECHNOLOGY, Daejeon (KR); SEOUL NATIONAL UNIVERSITY R&DB FOUNDATION, Seoul (KR)

(72) Inventors: Ki Sun Kwon, Daejeon (KR); Jeongi Choi, Daejeon (KR); Sung Sup Park, Daejeon (KR); Sun Gun Chung, Seoul (KR); Eun Soo Kwon, Daejeon (KR); Kwang-Pyo Lee, Daejeon (KR); Seung Min Lee, Daejeon (KR)

(73) Assignees: KOREA RESEARCH INSTITUTE OF BIOSCIENCE AND BIOTECHNOLOGY, Daejeon (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 15/758,595

(22) PCT Filed: Sep. 9, 2016

(86) PCT No.: PCT/KR2016/010209
§ 371 (c)(1),
(2) Date: Mar. 8, 2018

(87) PCT Pub. No.: WO2017/043935
PCT Pub. Date: Mar. 16, 2017

(65) Prior Publication Data
US 2018/0243235 A1 Aug. 30, 2018

(30) Foreign Application Priority Data
Sep. 9, 2015 (KR) .................. 10-2015-0127891

(51) Int. Cl.
*A61K 31/045* (2006.01)
*A61K 31/047* (2006.01)
*A23L 33/10* (2016.01)
*A23K 50/50* (2016.01)
*A23K 20/105* (2016.01)
*C12N 5/077* (2010.01)

(52) U.S. Cl.
CPC .......... *A61K 31/047* (2013.01); *A23K 20/105* (2016.05); *A23K 50/50* (2016.05); *A23L 33/10* (2016.08); *C12N 5/0658* (2013.01); *A23V 2002/00* (2013.01); *C12N 2500/30* (2013.01); *C12N 2501/999* (2013.01)

(58) Field of Classification Search
None
See application file for complete search history.

(56) References Cited

U.S. PATENT DOCUMENTS 4,639,469 A    1/1987  Corvi-Mora

FOREIGN PATENT DOCUMENTS

| KR | 10-2003-0047503 A | | 6/2003 |
|---|---|---|---|
| WO | 92/03128 A1 | | 3/1992 |
| WO | 98/55085 A1 | | 12/1998 |
| WO | WO 02051395 | * | 7/2002 |

OTHER PUBLICATIONS

H. Zeytinoglu et al., "Inhibition of DNA synthesis by Carvacrol in mouse myoblast cells bearing a human N-RAS oncogene", Phytomedicine, 2003, pp. 292-299, vol. 10, No. 4.
International Search Report for PCT/KR2016/010209, dated Jan. 12, 2017 (PCT/ISA/210).

* cited by examiner

*Primary Examiner* — Shobha Kantamneni
(74) *Attorney, Agent, or Firm* — Sughrue Mion, PLLC

(57) ABSTRACT

The present invention relates to sobrerol or a pharmaceutically acceptable salt thereof, which can promote differentiation of myoblasts to form myotubes, thereby preventing muscle weakness and effectively improving muscle functions. Therefore, the pharmaceutical composition containing the same can be effectively used for preventing or treating muscle weakness related diseases.

10 Claims, 11 Drawing Sheets

C2C12 myogenin luciferase

COMPOSITION FOR PREVENTING OR TREATING MUSCLE WEAKNESS-RELATED DISEASES COMPRISING SOBREROL

CROSS REFERENCE TO RELATED APPLICATIONS

This application is a National Stage of International Application No. PCT/KR2016/010209 filed Sep. 9, 2016, claiming priority based on Korean Patent Application No. 10-2015-0127891, filed Sep. 9, 2015.

TECHNICAL FIELD

The present invention relates to a composition for promoting differentiation of myoblasts comprising sobrerol or a pharmaceutically acceptable salt thereof, a pharmaceutical composition for preventing or treating a muscle weakness-related disease, a health functional food composition for preventing or improving a muscle weakness-related disease, a composition for increasing muscle strength, a feed or a feed additive for increasing muscle strength, a method for treating a muscle weakness-related disease comprising the step of administering a composition comprising sobrerol or a pharmaceutically acceptable salt thereof to an individual, a method for increasing muscle strength, comprising the step of administering a composition comprising sobrerol or a pharmaceutically acceptable salt thereof to an individual, a composition for improving wrinkles caused by muscle weakness, and a method for improving wrinkles caused by muscle weakness.

The present invention also relates to a method for promoting differentiation of myoblasts using sobrerol or a pharmaceutically acceptable salt thereof, and a method for producing differentiated myoblasts.

BACKGROUND ART

Diseases that cause muscle weakness include sarcopenia which progresses with aging, muscle atrophy caused by imbalance in protein metabolism or decrease in muscle uses, starvation, wasting diseases (cancer etc.), and acardiotrophy which progresses with aging.

Sarcopenia refers to a decrease in muscle strength due to a decrease in skeletal muscle mass during aging. Not only the decrease in skeletal muscle mass, which is the most important feature of sarcopenia, but also changes in the type of muscle fibers is observed. Type 1 and Type 2 decrease with aging at a similar rate, whereas Type 2 muscle fiber thickness does not change much but Type 1 muscle fiber thickness decreases significantly with sarcopenia. It has been reported that such sarcopenia causes aging and functional impairment among elderly people (Roubenoff R., Can. J. Appl. Physiol. 26, 78-89, 2001).

Although sarcopenia is caused by various factors, the research on each factor is still insufficient. It is caused by a reduction in growth hormone or a neurological change, a change in physical activity, a change in metabolism, an increase in a sex hormone level, fat or catabolic cytokines, and a change in the balance of protein synthesis and differentiation (Roubenoff R. and Hughes V A, J. Gerontol. A. Biol. Sci. Med. Sci. 55, M716-M724, 2000). A decrease in satellite cell activation is considered to be an important factor which causes a decrease in skeletal muscle mass which is the principal characteristic of sarcopenia. Satellite cells are small mononuclear cells located between the basement membrane and the sarcolemma of a muscle fiber. They are activated by stimulation, such as injury or exercise, to proliferate into myoblasts, and they fuse with other cells to form polynuclear muscle fibers as differentiation progresses. Thus, as the activity of satellite cells decreases, the capability of regenerating damaged muscle or the response to differentiation signals is reduced, resulting in decreased muscle formation.

Muscle atrophy is caused by nutritional deficiency or long-term muscle disuse, which is due to protein degradation by the breakdown of the normal balance of protein synthesis and degradation.

On the other hand, acardiotrophy is caused by starvation, wasting diseases (cancer, etc.), and senility, in which myocardial fibers become dry and thin and their nuclei get concentrated and vary in size. Thus, the volume of muscle fascicle and the whole heart get smaller, subepicardial adipose tissue is markedly decreased, and the coronary artery becomes bent. Brown wasting pigments (lipofuscin) appear around both ends of the nuclei of the myocardial fibers, and the whole heart gets brownish with the decrease of adipose tissue.

There are three main treatment methods for sarcopenia. The first is exercise. Exercise has been reported to increase skeletal muscle's protein synthesis in short term and increase muscle strength and motility of the elderly. However, it is unsuitable for a long-term treatment (Timothy J. Doherty, J. Appl. Physiol. 95, 1717-1727, 2003). The second is medication, and testosterone or anabolic steroid may be used, but it shows side effects such as inducing virilism in women and prostate symptoms in men, etc. Other approved therapeutic methods include DHEA (dehydroepiandrosterone) and growth hormone, which have been reported to be useful therapeutic methods at the sites that include SARMs (Selective Androgen Receptor Modulators) (D. D. Thompson, J. Musculoskelet Neuronal Interact 7, 344-345, 2007). Diet therapy is also known as a treatment method, but nutritional assessment shows that malnutrition or modern eating habits are unsuitable for maintaining a reasonable total body mass.

Recently, a stem cell therapy in which satellite cells are introduced into the body after the cells are isolated and differentiated in vitro, and a method for maintaining or strengthening muscles by directly activating satellite cells in the body to promote myogenesis have been introduced as the treatment methods for muscle weakness such as sarcopenia. (Shihuan Kuang and Michael A. Rudnicki, Trends in Molecular Medicine 14, 82-91, 2008).

Accordingly, in order to treat a muscle weakness-related disease, a method for differentiating muscle cells with a more fundamental method not inducing side effects is required, and thus it is necessary to develop a substance capable of promoting differentiation of myoblasts.

Disclosure of Invention

Technical Problem

The present inventors have made intensive efforts to develop a therapeutic agent for a muscle weakness-related disease that increases muscle mass and effectively recovers muscular function by promoting differentiation of myoblasts, and as a result, found that sobrerol promotes differentiation of myoblasts and thus can be used for prevention and treatment of a muscle weakness-related disease, and completed the present invention.

Solution to Problem

An object of the present invention is to provide a composition for promoting differentiation of myoblasts.

Another object of the present invention is to provide a method for promoting differentiation of myoblasts.

Still another object of the present invention is to provide a preparation method of differentiated myoblasts.

Still another object of the present invention is to provide a pharmaceutical composition for preventing or treating a muscle weakness-related disease.

Still another object of the present invention is to provide a health functional food composition for preventing or improving a muscle weakness-related disease.

Still another object of the present invention is to provide a composition for increasing muscle strength.

Still another object of the present invention is to provide a feed or a feed additive for increasing muscle strength.

Still another object of the present invention is to provide a method for treating a muscle weakness-related disease comprising the step of administering a composition comprising sobrerol or a pharmaceutically acceptable salt thereof to an individual.

Still another object of the present invention is to provide a method for increasing muscle strength, comprising the step of administering a composition comprising sobrerol or a pharmaceutically acceptable salt thereof to an individual.

Still another object of the present invention is to provide a composition for improving wrinkles caused by muscle weakness.

Still another object of the present invention is to provide a method for improving wrinkles caused by muscle weakness, comprising the step of administering a composition comprising sobrerol or a pharmaceutically acceptable salt thereof to an individual.

Advantageous Effects of Invention

Sobrerol or a pharmaceutically acceptable salt thereof according to the present invention can promote differentiation of myoblasts to form myotubes, and thus it can not only prevent muscle weakness but effectively improve muscle functions. Therefore, a pharmaceutical composition comprising the same can be effectively used for preventing or treating a muscle weakness-related disease.

BEST MODE FOR CARRYING OUT THE INVENTION

In order to achieve the above object, one embodiment of the present invention provides a composition for promoting differentiation of myoblasts, comprising sobrerol or a pharmaceutically acceptable salt thereof.

As used herein, the term "sobrerol" is one of the terpene alcohols having the formula $C_{10}H_{18}O_2$, wherein the terpene is a flammable, unsaturated hydrocarbon which encompasses the carbohydrates having the formula $(C_5H_8)n$ and derivatives thereof such as alcohols, aldehydes, ketones, etc.

The term "pharmaceutically acceptable salt" as used herein refers to a formulation of a compound that does not cause serious irritation to an organism to which the compound is administered and does not impair the biological activity and properties of the compound. The pharmaceutical salt may be an acid addition salt formed with an acid such as an inorganic acid, e.g., hydrochloric acid, sulfuric acid, nitric acid, phosphoric acid, hydrobromic acid, hydroiodic acid, etc., an organic carboxylic acid, e.g., tartaric acid, formic acid, citric acid, acetic acid, trichloroacetic acid, trifluoroacetic acid, gluconic acid, benzoic acid, lactic acid, fumaric acid, maleic acid, salicylic acid, etc., and an sulfonic acid, e.g., methanesulfonic acid, ethanesulfonic acid, benzenesulfonic acid, p-toluenenesulfonic acid, etc. For example, the pharmaceutically acceptable carboxylic acid salts include metal salts or alkaline earth metal salts formed with lithium, sodium, potassium, calcium, magnesium, etc, amino acid salts such as lysine, arginine and guanidine, and organic salts such as dicyclohexylamine, N-methyl-D-glucamine, tris(hydroxymethyl) methylamine, diethanolamine, choline and triethylamine, etc.

As used herein, the term "myoblast differentiation" refers to a process in which mononuclear myoblasts form myotubes through fusion. Myoblasts, which correspond to muscle precursor cells, exhibit Pax7+ markers in case of self-renewal and Pax7+/MyoD+ in case of proliferation. The cells at a differentiation stage that form the myotube can be distinguished using Pax7−, MHC+, Troponin C+, and myogenin+ markers.

Figure 2:
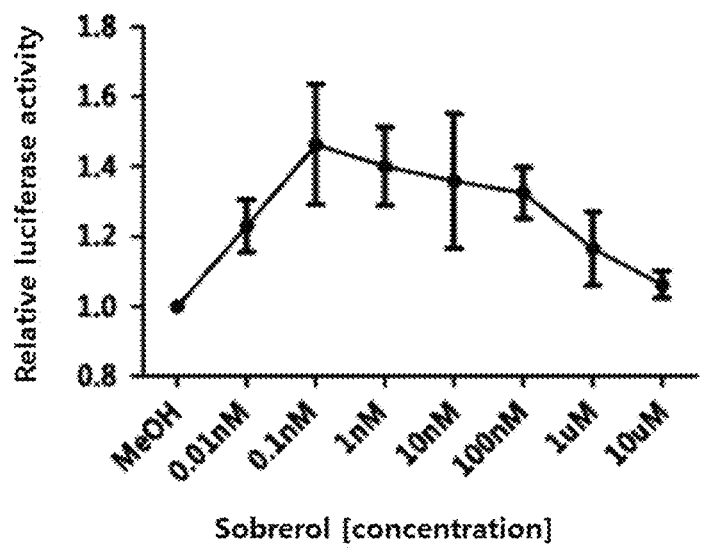
FIG. 2 is a graph showing luciferase activity at each concentration when myoblasts transformed with vectors for luciferase assay were treated with sobrerol.

In one embodiment of the present invention, by verifying the luciferase activity of sobrerol in relation to the promoter activity of myogenin, it was verified that the sombrero had an excellent capability of promoting differentiation of muscles (FIG. 2).

Specifically, one embodiment of the present invention relates to a composition for promoting differentiation of myoblasts, wherein the concentration of sobrerol ranges from 0.01 nM to 1 µM. The composition may be a serum-containing DMEM differentiation medium, but any medium or composition capable of promoting differentiation of myoblasts may be included without limitation. In the above composition, sobrerol may be contained at a concentration of 0.05 nM to 100 nM, specifically, 0.1 nM to 10 nM, but is not limited thereto. In addition, the composition may further comprise additional substances necessary for cell culture or differentiation.

As used herein, the composition may be one that increases the level of mRNA of a myogenic regulatory factor or a protein expressed by the mRNA.

The term "myogenic regulatory factor" as used herein refers to a basic helix-loop-helix (bHLH) transcription factor, which is a factor that plays the role of regulating muscle production. The basic helix-loop-helix refers to the protein structural motif that is characteristic of the transcription factor family, and is distinguished from helix-turn-helix.

One embodiment of the present invention relates to a composition for promoting differentiation of myoblasts wherein the myogenic regulatory factor is one selected from the group consisting of MyoD, myogenin, and myosin heavy chain (MyHC).

Figure 3:
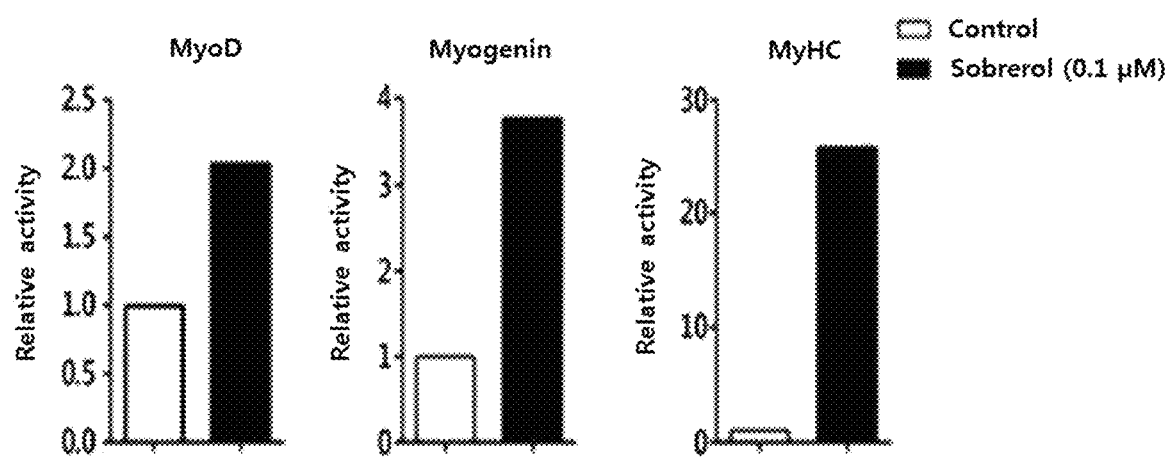
FIG. 3 provides graphs showing mRNA of the myogenic regulation factors, MyoD, myogenin, and myosin heavy chain (MyHC) when myoblasts were treated with 0.1 μM of sobrerol.
Figure 4:
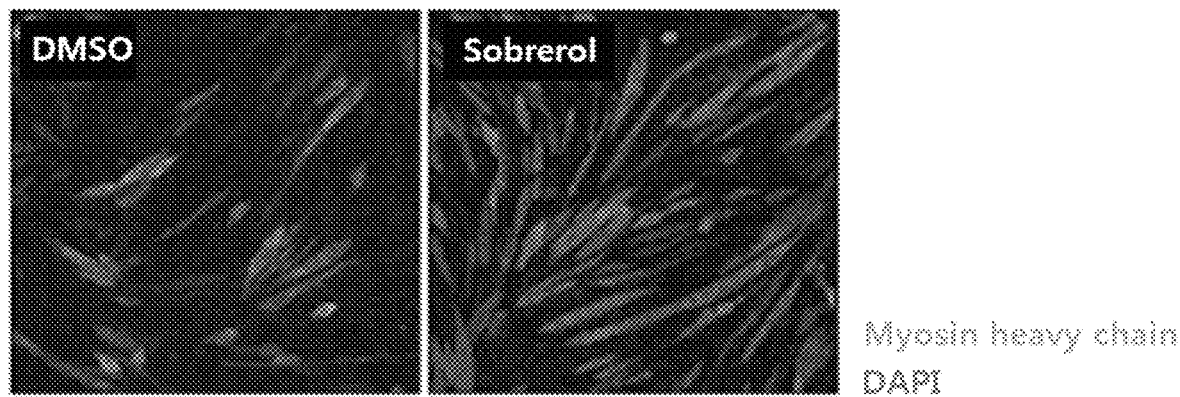
FIG. 4 shows protein expression levels of myosin heavy chain when the myoblasts were treated with 0.1 μM of sobrerol.

In one embodiment of the present invention, it was verified by qRT-PCR that sobrerol can increase the mRNA of MyoD, myogenin, and myosin heavy chain (MyHC) (FIG. 3). Also, in one embodiment of the present invention, it was verified by immunofluorescence that sobrerol can increase the protein expression of myosin heavy chain (FIG. 4).

Meanwhile, the mRNA can be analyzed by RT-PCR, quantitative real time PCR, competitive RT-PCR, real time quantitative RT-PCR, RNase protection analysis (RPA), Northern blotting, DNA chip analysis, etc., but the present invention is not limited thereto.

In addition, the level of the protein may be determined by western blotting, enzyme linked immunosorbent assay (ELISA), radioimmunoassay (RIA), radioimmunodiffusion, Ouchterlony immunodiffusion, rocket immunoelectrophoresis, immunohistochemical staining, immunoprecipitation Assay, complement fixation assay, immunofluorescence, immunochromatography, fluorescence activated cell sorter analysis (FACS), and protein chip technology assay, etc., but the present invention is not limited thereto.

In another embodiment of the present invention, there is provided a method for promoting differentiation of myoblasts, comprising the step of treating myoblasts with sobrerol or a pharmaceutically acceptable salt thereof.

Specifically, the myoblasts may be isolated myoblasts.

In one embodiment of the present invention, luciferase activities in the group treated with sobrerol and the group not treated with sobrerol were compared, and it was found that the luciferase activity in the group treated with sobrerol was excellent (FIG. 2), and thus the step of treating myoblasts with sobrerol is an essential step for promoting differentiation of the myoblasts.

In another embodiment of the present invention, there is provided a preparation method of differentiated myoblasts, comprising the step of treating myoblasts with the sobrerol or a pharmaceutically acceptable salt thereof to differentiate the myoblasts.

The sobrerol or a pharmaceutically acceptable salt thereof is as described above.

Specifically, the myoblasts may be isolated myoblasts.

In another embodiment of the present invention, there is provided a pharmaceutical composition for preventing or treating a muscle weakness-related disease, comprising sobrerol or a pharmaceutically acceptable salt thereof.

The concentration of sobrerol is as described above.

As used herein, the term "muscle weakness" refers to a state in which the strength of one or more muscles is reduced. The muscle weakness may be limited to one muscle, one side of the body, upper or lower extremity, or may appear throughout the body. In addition, subjective muscle weakness symptoms, including muscle fatigue and myalgia, can be quantified in an objective way through medical examinations.

As used herein, the term "muscle weakness-related disease" refers to any disease that may be caused by muscle weakness, such as, for example, sarcopenia, muscle atrophy, muscular dystrophy, acardiotrophy, or the like, but is not limited thereto.

Accordingly, the composition of the present invention can be used for the preventing or treating sarcopenia, muscle atrophy, muscular dystrophy, acardiotrophy by promoting differentiation of myoblasts.

Specifically, sarcopenia in the present invention refers to a gradual decrease in skeletal muscle mass due to aging, directly leading to a decrease in muscle strength, which may result in a decrease in various body functions and a disorder.

In addition, muscle atrophy is a disease in which muscles of the limbs gradually become atrophied in bilateral symmetry, causing progressive denaturation of the motor nerve fibers and cells in the spinal cord, which may induce amyotrophic lateral sclerosis (ALS) and spinal progressive muscular atrophy (SPMA).

Muscular dystrophy is a disease in which gradual muscle atrophy and muscle weakness develop, which refers to degenerative myopathy characterized by necrosis of muscle fibers pathologically. Muscle cell membrane damage leads to muscle fiber necrosis and degeneration, which cause muscle weakness and atrophy.

Muscular dystrophy can be subdivided according to the extent and distribution of muscle weakness, the age at onset, the rate of progression, the severity of symptoms, and family history, and non-limiting examples of the muscular dystrophy include Duchenne muscular dystrophy, Becker muscular dystrophy, limb-girdle muscular dystrophy, Emery-Dreifuss muscular dystrophy, facioscapulohumeral muscular dystrophy, myotonic dystrophy, myotonic muscular dystrophy, oculopharyngeal muscular dystrophy, distal muscular dystrophy, and congenital muscular dystrophy.

Acardiotrophy in the present invention is a disease in which the heart becomes atrophied by an external or internal factor, which may show brownish atrophy where myocardial fibers become dry and thin found which can be found in starvation, wasting diseases, and senility.

As used herein, the term "prevention" refers to any action that inhibits or slows down the onset of a muscle weakness-related disease by the administration of the composition.

As used herein, the term "treatment" refers to any action that improves or alleviates a symptom due to a muscle weakness-related disease by administration of the composition.

A pharmaceutical composition of the present invention may contain, for administration, a pharmaceutically acceptable carrier, excipient or diluent in addition to the above-mentioned sobrerol or a pharmaceutically acceptable salt thereof. Examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil.

A pharmaceutical composition of the present invention may be prepared into a pharmaceutical formulation using methods well known in the art so as to provide rapid, sustained, or delayed release of sobrerol or a pharmaceutically acceptable salt thereof. In the preparation of the formulation, it is preferred that the active ingredient is mixed or diluted with a carrier, or enclosed in the carrier in the form of a container.

In addition, a pharmaceutical composition of the present invention can be applied to any formulation, but is preferably prepared for parenteral use. The parenteral formulation may be one for injection, application, or a spray type such as aerosol.

Formulations for parenteral administration include sterile aqueous solutions, non-aqueous solvents, suspensions, emulsions, freeze-dried preparations, and suppositories. For the non-aqueous solvents and suspensions, propylene glycol, polyethylene glycol, vegetable oils such as olive oil, injectable esters such as ethyl oleate, etc., may be used.

To formulate into an injection type formulation, sobrerol or a pharmaceutically acceptable salt thereof may be prepared as a solution or a suspension by mixing with a stabilizer or a buffer in water, and may be formulated as a dosage unit of an ampule or a vial.

A pharmaceutical composition comprising sobrerol or a pharmaceutically acceptable salt thereof of the present invention can be directly injected into a site which requires enhancement of muscle strength of an individual who has developed a muscle weakness-related disease or has a potential for developing the disease, where differentiated myoblasts can be prepared by applying to the myoblasts in vivo and in vitro and then injected into the site which requires enhancement of muscle strength of the individual who has developed a muscle weakness-related disease or has a potential for developing the disease.

Further, the composition may comprise additional ingredients, for example, substances known as therapeutic agents for a muscle weakness-related disease, as long as they do not interfere with the preventing or treating a muscle weakness-related disease by sobrerol or a pharmaceutically acceptable salt thereof.

Figure 7:
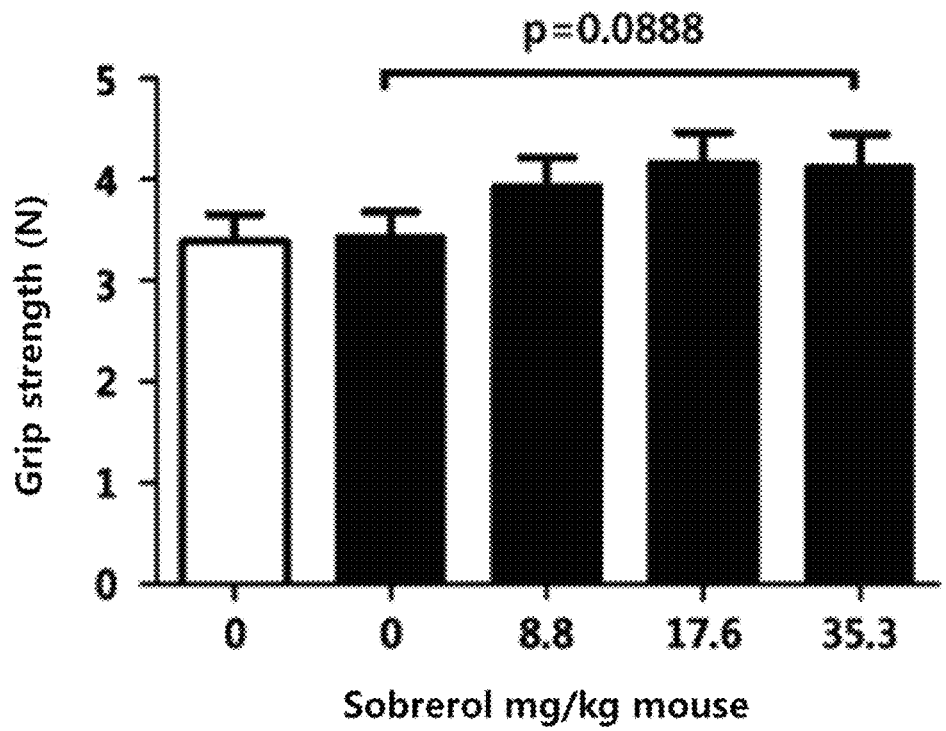
FIG. 7 is a graph showing the effect of increasing muscle strength at each administration concentration as a result of a grip strength test after administering sobrerol to the mice with muscle weakness.
Figure 10:
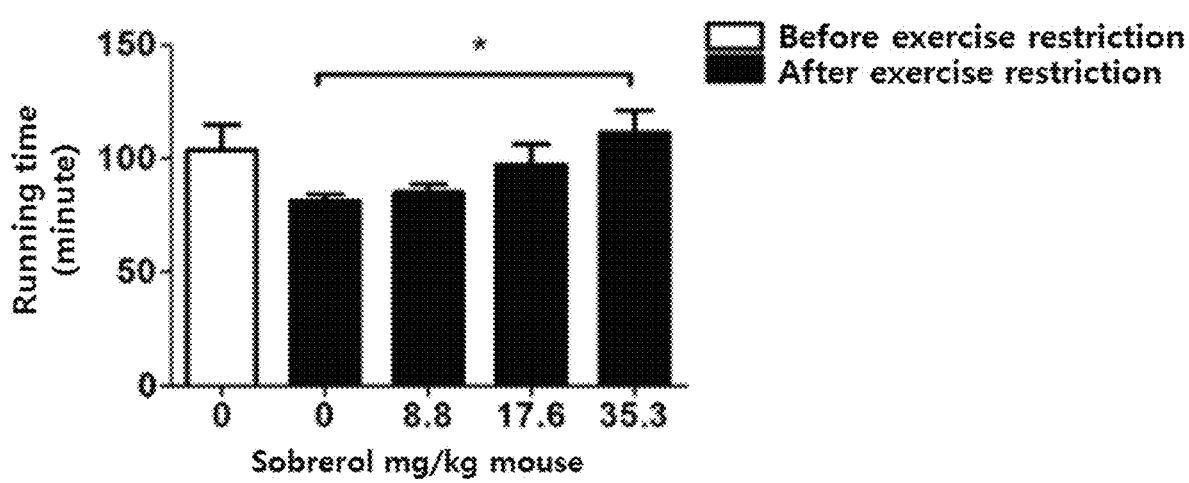
FIG. 10 is a graph showing the effect of restoring damaged muscles at each administration concentration as a result of a treadmill test after administering sobrerol to the mice with muscle weakness.

Specifically, a pharmaceutical composition of the present invention can promote differentiation of myoblasts. In one embodiment of the present invention, after myoblasts were treated with sobrerol, mRNA of myogenic regulatory factor related to muscle cell differentiation was evaluated by qRT-PCR, and it was verified that the effect of promoting muscle cell differentiation was very high (FIG. 3). In addition, both hind limbs of mice were immobilized for 10 days, and then allowed to move again for 3 days, followed by a grip strength test and a treadmill test, and as a result, it was verified that the grip strength measurement values were higher and the running time was longer in the group treated with sobrerol (FIGS. 7 and 10). These results indicated that sobrerol has the effect of increasing muscle strength and restoring damaged muscles.

These results indicated that sobrerol or a pharmaceutically acceptable salt thereof is effective in promoting differentiation of myoblasts and may be useful for prevention and treatment of a muscle weakness-related disease.

Another embodiment of the present invention provides a health functional food composition for preventing or improving a muscle weakness-related disease, comprising sobrerol or a pharmaceutically acceptable salt thereof. The composition of the present invention can be used with a medication for treating the disease simultaneously or separately, before or after the onset of the muscle weakness-related disease, to prevent or improve the muscle weakness-related disease.

The muscle weakness-related disease refers to all diseases that may develop due to muscle weakness, for example, sarcopenia, muscle atrophy, muscular dystrophy, and acardiotrophy, but is not limited thereto. Preferably, the health functional food composition can promote differentiation of myoblasts.

As used herein, the term "improvement" refers to all actions that at least reduce a parameter related to the condition being treated, such as, for example, the degree of a symptom.

Also, when a health functional food composition of the present invention is used as a food additive, the composition may be added as it is, or may be used with other food or food ingredients, and may be suitably used according to a conventional method. Generally, the composition of the present invention may be added in an amount of 15% by weight or less, preferably 10% by weight or less, based on the raw material in the preparation of food or beverages. However, in the case of long-term intake for the purpose of health and hygiene or for the purpose of controlling health, the amount may be less than the above range, and since there is no problem in terms of safety, the active ingredient may be used in an amount exceeding the above range.

There is no particular limitation of the kind of the food. Examples of the food to which the above substance can be added include meats, sausages, bread, chocolates, candies, snacks, confectionery, pizza, ramen, other noodles, gum, dairy products including ice cream, various soups, beverages, teas, drinks, alcoholic beverages and multi-vitamin preparations, and any health functional food in a conventional meaning can be included.

The health beverage composition of the present invention may contain various flavors or natural carbohydrates as additional ingredients as with conventional beverages. For the above natural carbohydrates, a monosaccharide, e.g., glucose, fructose, etc., a disaccharide, e.g., maltose, sucrose, a natural flavor, e.g., dextrin, cyclodextrin, or a synthetic flavor, e.g., saccharin, or aspartame, etc. may be used. The ratio of the natural carbohydrates can be appropriately determined by a person skilled in the art.

In addition, a composition of the present invention may further contain various nutrients, vitamins, electrolytes, flavoring agents, colorants, pectic acid or its salt, alginic acid or its salt, organic acids, protective colloidal thickeners, pH adjusters, stabilizers, preservatives, glycerin, alcohol, carbonating agents used in carbonated drinks, etc. Additionally, the composition of the present invention may contain fruit flesh for the preparation of natural fruit juices, fruit juice beverages and vegetable juices. These components may be used alone or in combination. The ratios of these additives can also be appropriately selected by a person skilled in the art.

Another embodiment of the present invention provides a composition for increasing muscle strength, comprising sobrerol or a pharmaceutically acceptable salt thereof.

The term "increasing muscle strength" as used herein refers to strengthening body performance, strengthening maximum endurance, increasing muscle mass, strengthening muscle recovery, reducing muscle fatigue, improving energy balance, or a combination thereof.

A composition for increasing muscle strength comprising sobrerol or a pharmaceutically acceptable salt thereof can increase the total muscle mass by increasing muscle mass through the capability of differentiating the myoblasts into muscle cells, thereby strengthening maximum endurance, enhancing body performance and reducing muscle fatigue. In addition, muscle injury can be rapidly cured since muscle cells can be replaced quickly.

A composition for increasing muscle strength of the present invention may contain, for administration, a pharmaceutically acceptable carrier, excipient or diluent in addition to the above-mentioned sobrerol or a pharmaceutically acceptable salt thereof. The pharmaceutically acceptable carrier, excipient or diluent is as described above.

In one embodiment of the present invention, mice were treated with the sobrerol, and both hind limbs of the mice were immobilized for 10 days, and then allowed to move again for 3 days, and then subjected to a grip strength test and a treadmill test. As a result, it was verified that the measured value of grip strength increased and the running time was longer in the experimental group administered with sobrerol (FIGS. 7 and 10).

As used herein, the composition may be one which can increase muscle size or weight.

In one embodiment of the present invention, it was verified by immunofluorescence analysis and muscle fiber diameter measurement that muscle size and weight increased in the mice treated with sobrerol in model mice as well as in aged mice as compared to the control group (FIGS. 11, 12, 15 and 16).

One embodiment of the present invention provides a feed or a feed additive for increasing muscle strength, comprising sobrerol or a pharmaceutically acceptable salt thereof.

As used herein, "feed" refers to a substance that supplies organic or inorganic nutrients necessary for maintaining animal life. The feed includes nutrients such as energy, protein, lipid, vitamins and minerals required by animals such as livestock, and may be a vegetable feed, such as grains, roots/fruits, food processing byproducts, algae, fibers, oils and fats, starches, gourds, and grain byproducts; and an animal feed, such as proteins, inorganic materials, oils and fats, minerals, single-cell proteins, etc., but is not limited thereto.

As used herein, the term "feed additive" refers to a substance to be added to the feed to improve the productivity or health of an animal, which includes, but is not limited to, amino acids, vitamins, enzymes, flavors, silicate agents, buffering agents, extracting agents, oligosaccharides, etc.

The content of sobrerol or a pharmaceutically acceptable salt thereof comprised in the feed or the feed additive of the present invention is not particularly limited, but may range from 0.001 to 1% (w/w), preferably 0.005 to 0.9% (w/w), and most preferably 0.01 to 0.5% (w/w).

Another embodiment of the present invention provides a method for treating a muscle weakness-related disease, comprising the step of administering a composition comprising sobrerol or a pharmaceutically acceptable salt thereof to an individual.

Another embodiment of the present invention provides a method for increasing muscle strength, comprising the step of administering a composition comprising sobrerol or a pharmaceutically acceptable salt thereof to an individual.

The term "individual" as used herein refers to all animals, including mammals including rats, livestock, humans, etc.

The term "administering" as used herein collectively refers to providing a certain substance to an individual by any suitable method, and the administration route may be any conventional route so long as the substance can reach a targeted skin.

The muscle weakness-related disease is as described above.

In one embodiment of the present invention, it has been found that when the sobrerol was administered to mice, it enhances muscle strength of the mice and increases the size and weight of the muscles, and thus a composition comprising sobrerol or a pharmaceutically acceptable salt thereof can be used in the treatment of a muscle weakness-related disease (FIGS. 10 to 16).

Another embodiment of the present invention provides a composition for improving wrinkles caused by muscle weakness, comprising sobrerol or a pharmaceutically acceptable salt thereof.

Another embodiment of the present invention provides a method for improving wrinkles caused by muscle weakness, comprising the step of administering or applying a composition comprising sobrerol or a pharmaceutically acceptable salt thereof to an individual.

As used herein, "muscle weakness" is as described above.

As used herein, "wrinkle" refers to a phenomenon in which skin is wound or folded due to the reduction of skin elasticity caused by aging of skin, decrease in muscle mass, etc. The bending of the skin that forms the wrinkle is affected by muscle exercises, and specifically, in the case of a face, bendings around eyes or those starting from the nose downward to the mouth may occur, which may be caused not only by repeated facial expressions with facial muscle exercise, but also drooping of the skin by gravity, not using facial muscles much, or decrease in the muscle mass or muscle strength with aging.

A composition for improving wrinkles, comprising sobrerol or a pharmaceutically acceptable salt thereof according to the present invention not only promotes differentiation of muscle cells (FIGS. 2 and 3), but also has the effect of increasing muscle strength and promoting recovery of injured muscles (FIGS. 7, 10, 13, and 14) and exhibits an effect of increasing the size and weight of muscles (FIGS. 11, 12, 15 and 16), thereby inducing the cell differentiation, enhancement of muscle strength, and recovery of elasticity of facial muscles, and thus the composition can improve skin wrinkles closely related thereto.

Specifically, the above-mentioned composition may be a pharmaceutical composition, a health functional food composition, or a cosmetic composition, and the pharmaceutical composition and the health functional food composition are as described above.

A cosmetic composition for improving skin wrinkles according to the present invention may be in the form of a cream, a lotion, an essence, a gel, an ointment, a foam, a face lotion, a pack, an emollient lotion, an emulsion, a foundation, a makeup base, a soap, a liquid cleansing agent, a bath preparation, a sun screen cream, or a sun oil, etc.

A cosmetic composition for improving skin wrinkles according to the present invention may further comprise at least one additive selected from the group consisting of water, a surfactant, a moisturizer, a 16-4 lower alcohol, a chelating agent, a bactericide, an antioxidant, an antiseptic, an antioxidant, a preservative, a pigment, and a flavoring agent.

DETAILED DESCRIPTION OF THE INVENTION

Mode for the Invention

Hereinafter, constitutions and effects the present invention will be described in detail with reference to Examples. However, the following Examples are merely intended to illustrate the present invention and the scope of the present invention is not limited by the following Examples.

Example 1: Verification of Myoblast Differentiation-Promoting Capability of Sobrerol Using Secreted Luciferase Reporter System

Figure 1:
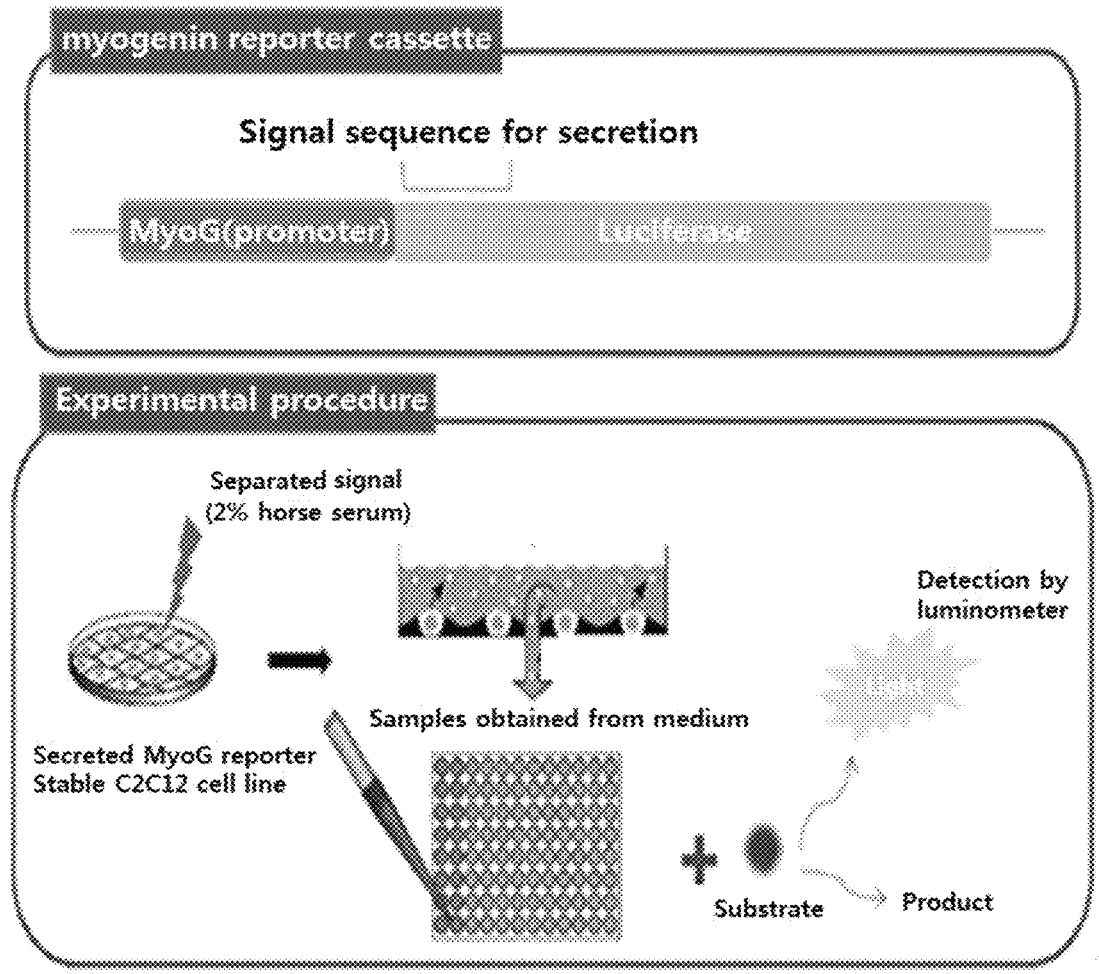
FIG. 1 is a photograph schematically showing the structure of a myogenin reporter cassette for evaluating the capability of promoting myogenesis, and an experimental procedure.

Example 1-1: Preparation of Myoblast Line C2C12 Expressing Luciferase Enzyme and Method for Verifying Promotion of Myogenesis To evaluate the myoblast differentiation-promoting capability of sobrerol, a secreted MyoG luciferase assay system was used (FIG. 1).

Specifically, the promoter portion of myogenin, which is a protein whose expression is increased upon myogenesis, was cloned into a secreted luciferase vector (pMetLuc2-Reporter Vector, Clontech), and then the vector was transfected into myoblasts C2C12 to prepare a myogenin promoter-secreted luciferase C2C12 myoblast line capable of stably expressing the luciferase enzyme The differentiation degree of the myoblasts into myotube cells can be quantitatively verified through the system in which the luciferase enzymes are secreted into the medium as the myogenin promoter is activated. To induce differentiation into muscle cells, DMEM (Dulbecco's Modified Eagle Medium, Invitrogen) medium supplemented with 2% horse serum was added to the C2C12 myoblasts. Herein, the expressed MEF2 and MyoD bind to the myogenin promoter, and then the luciferase enzymes are expressed and secreted out of the cell. Since the secreted luciferase enzymes are present in the medium, it can be measured to verify the degree of myogenesis.

Example 1-2: Verification of Muscle Cell Differentiation-Promoting Capability of Sobrerol The myoblast differentiation-promoting capability was verified using sobrerol at each concentration in the range of 0.1 nM to 10 µM. Specific experimental methods are as follows.

On the first day, the C2C12 cells prepared in the Example 1-1 were inoculated into a 96-well plate containing DMEM medium supplemented with 10% bovine serum (FBS) at a concentration of $5 \times 10^3$ cells/well. In the morning of the second day, the medium of the well plate was replaced with DMEM medium (Growth medium, GM) supplemented with 10% bovine serum, which is the same component. In the afternoon, the medium (GM) was collected. Then, each well was treated with 100 µL of DMEM medium (differentiation medium 1, DM1) supplemented with 2% horse serum diluted with the sobrerol at each concentration. On the third day, the DM1 medium was collected, and the wells were treated with the same medium as in the second day (DM2). On the fourth day, the DM2 was collected.

The media containing the luciferase secreted in the differentiation process of C2C12 cells were collected starting from the growth medium (GM) to the first day differentiation medium (DM1) and the second day differentiation medium (DM2) as described above, and 5 µL of coelenterazine as a substrate was added to 50 µL of the collected medium containing the luciferase enzyme, and the generated light was measured using a luminometer. The myogenesis-promoting capability of sobrerol at each concentration was measured through digitization by subtracting the measured values of DM0 from the measured values of DM1 and DM2. When the value of the negative control group treated with methanol (MeOH) was set at 1, the increase and decrease values of the experimental group treated with sobrerol were compared, to evaluate the myogenesis-promoting capability of sobrerol. Ready-To-Glow™ Secreted Luciferase Reporter Systems (Clontech) was used as the luciferase assay kit, and the experiment was repeated three times.

As a result of the evaluation, the luciferase activity increased 1.2-fold or higher even in the case of treatment with 0.01 nM low concentration sobrerol as compared to the negative control. In addition, the groups treated with 0.01 nM to 10 µM of sobrerol showed higher luciferase activity than the control group, and in particular, the luciferase activity increased about 1.5-fold at the concentration of 0.1 nM (FIG. 2).

Accordingly, it was verified that the differentiation of muscle cells can be promoted even by low concentration of sobrerol, and in particular, the greatest differentiation-promoting capability was observed at the concentration of 0.1 nM.

Example 2: Levels of mRNA of Myogenic Regulatory Factor and Protein Expressed by the mRNA

Example 2-1: Verification of mRNA Level of the Myogenic Regulatory Factor

Experiments were conducted to verify the effect of sobrerol on mRNA of myogenic regulatory factor. Specifically, the myoblasts (C2C12 myoblast cells) placed in the growth medium were treated with 0.1 µM sobrerol for 48 hours, and then subjected to qRT-PCR to measure the levels of MyoD, myogenin, and myosin heavy chain (MyHC).

The experiment results showed that mRNA of the myogenic regulatory factors MyoD, myogenin, and myosin heavy chain (MyHC) increased in the sobrerol-treated myoblast group. Specifically, MyoD and myogenin increased 2-fold and 4-fold, respectively, and myosin heavy chain increased about 25-fold or higher (FIG. 3). These results indicated that sobrerol has myogenesis-promoting capability.

Example 2-2: Verification of Expression Level of Myosin Heavy Chain Protein Among the myogenic regulatory factors whose mRNA increased in the Example 2-1, experiments were conducted to verify the effect of sobrerol on the expression of myosin heavy chain. Specifically, the expression level of the myosin heavy chain protein was measured by immunofluorescence after treating the C2C12 myoblasts placed in the differentiation medium with 0.1 µM of sobrerol for 72 hours.

As a result of the measurement, it was verified that fluorescence intensity in the myoblast group treated with sobrerol was stronger than the group treated with DMSO (FIG. 4). These results indicated that sobrerol has myogenesis-promoting capability.

Example 3: Verification of Restoring Effect of Sobrerol on Damaged Muscle Cells

Figure 5:
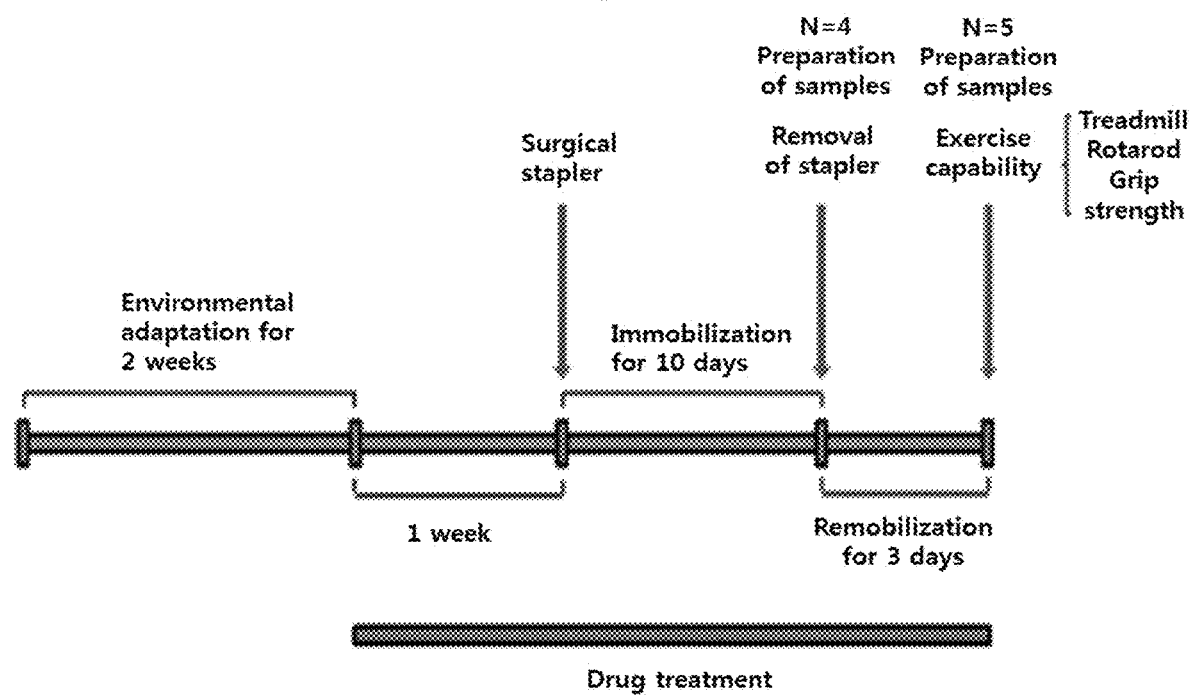
FIG. 5 is a schematic diagram showing an experiment for verifying the improvement of exercise capability of mice by treatment with sobrerol.

Example 3-1: Experiment Preparation for Verifying Improvement of Exercise Capability of Animals A total of 45 male C57BL/6 mice at 5 weeks of age (Daehan BioLink) were used in this animal experiment. The overall scheme is as shown in FIG. 5. After 2 weeks of adaptation to the surrounding environment, sobrerol was orally administered twice daily since 7 weeks of age. The control group was administered with 200 μL of water/20 g of mouse, and sobrerol was orally administered at a ratio of 1:2:4 [8.8 mg/200 μL/20 g (mouse), 17.6 mg/200 μL/20 g (mouse) and 35.3 mg/200 μL/20 g (mouse)] to verify dose dependency. At 8 weeks of age, both hind limbs of the mice were immobilized for 10 days using a surgical stapler (Autosuture Royal 35W stapler). (A novel hindlimb immobilization procedure for studying skeletal muscle atrophy and recovery in mouse. J Appl Physiol 106: 2049-2059, 2009). After removing the surgical stapler, they were allowed to move again for 3 days (remobilization), and then exercise capability improvement-verification tests (treadmill, and grip tests) were conducted.

On the other hand, the oral doses of sobrerol for mice were converted into oral doses of humans as following (Tables 1 to 3) (Guidance for Industry Estimating the Maximum Safe Starting Dose in Initial Clinical Trials for Therapeutics in Adult Healthy Volunteers. July 2005 Pharmacology and Toxicology).

TABLE 1

Conversion of Animal Doses to Human Equivalent Doses Based on Body Surface Area

| | Reference | | | To Convert Dose in | To Convert Animal Dose in mg/kg to HED in mg/kg. Either | |
|---|---|---|---|---|---|---|
| | Body Weight (kg) | Working Weight Range (kg) | Body Surface Area (m²) | mg/kg to Dose in mg/m² Multiply by $k_{in}$ | Divide Animal Dose By | Multiply Animal Dose By |
| Species | | | | | | |
| Human | 60 | — | 1.62 | 37 | — | — |
| Child | 20 | — | 0.80 | 25 | — | — |
| Mouse | 0.020 | 0.011-0.034 | 0.007 | 3 | 12.3 | 0.081 |
| Hamster | 0.080 | 0.047-0.157 | 0.016 | 5 | 7.4 | 0.135 |
| Rat | 0.150 | 0.080-0.270 | 0.025 | 6 | 6.2 | 0.162 |
| Ferret | 0.300 | 0.160-0.540 | 0.043 | 7 | 5.3 | 0.189 |
| Guinea pig | 0.400 | 0.208-0.700 | 0.05 | 8 | 4.6 | 0.216 |
| Rabbit | 1.8 | 0.9-3.0 | 0.15 | 12 | 3.1 | 0.324 |
| Dog | 10 | 5-17 | 0.50 | 20 | 1.8 | 0.541 |
| Primates: | | | | | | |
| Monkeys | 3 | 1.4-4.9 | 0.25 | 12 | 3.1 | 0.324 |
| Manmoset | 0.350 | 0.140-0.720 | 0.06 | 6 | 6.2 | 0.162 |
| Squirrel monkey | 0.600 | 0.290-0.970 | 0.09 | 7 | 5.3 | 0.189 |
| Baboon | 12 | 7-23 | 0.60 | 20 | 1.8 | 0.541 |
| Micro-pig | 20 | 10-33 | 0.74 | 27 | 1.4 | 0.730 |
| Mini-pig | 40 | 25-64 | 1.14 | 35 | 1.1 | 0.946 |

HED = animal dose in mg/kg × animal weight in kg/human weight in kg
Human constant $K_{mhuman}$ and mouse constant $K_{mmouse}$ are 37 and 3, respectively.

TABLE 2

| Division method | calculation | |
|---|---|---|
| NOAEL | mg/kg ÷ [$k_{mhuman}/k_{manimal}$] | HED |
| 15 mg/kg in dogs | 15 mg/kg ÷ 1.8 = | 8 mg/kg |
| 50 mg/kg in rats | 50 mg/kg ÷ 6.2 = | 8 mg/kg |
| 50 mg/kg in monkeys | 50 mg/kg ÷ 3.1 = | 16 mg/kg |

[NOAEL (no-observed-adverse-effect-level)] ÷ [$k_{mhuman}/k_{mmouse}$] = human equivalent dose (HED), wherein an oral dose for mouse can be converted into an oral dose for human by dividing the oral dose for mouse by 12.3 ($k_{mhuman}/k_{mmouse}$ = 37/3).

The oral doses of sobrerol for human (70 kg) can be calculated by converting the oral doses for mouse (20 g) as follows (Table 3).

TABLE 3

| Mouse(mg/kg) | Human(mg/70 kg) |
|---|---|
| 8.8 | 50 |
| 17.6 | 100 |
| 35.3 | 200 |

Example 3-2: Grip Strength Test

Figure 6:
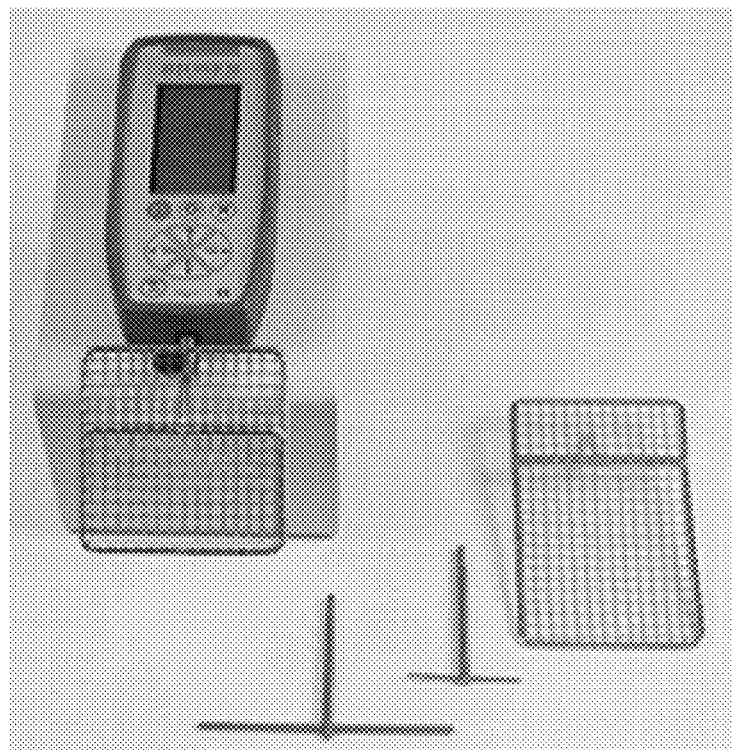
FIG. 6 is a photograph of a device for conducting a grip strength test.

The grip strength was measured using a grip strength measuring device for mouse (BIOSEB) (FIG. 6). Specifically, the front limbs of the mice of the Example 3-1 were placed on a wire net attached to an instrument panel capable of monitoring the strength, and the strength to hold the wire net was measured while the tail was gripped and pulled downward. The test was repeated three times in succession.

As a result of the grip strength test, the negative control group treated with distilled water showed a measurement value of 3.5 N or less, which was almost the same as that of the group in which exercise of the hind limbs were not restricted (non-immobilization group). On the other hand, the group orally administered with sobrerol showed a measurement value of 4.0 N or more. In addition, the measurement value of grip strength showed increasing tendency as higher concentration of sobrerol was administered (FIG. 7). These results indicated that sobrerol had the effect of increasing muscle strength.

Example 3-3: Treadmill Test

Figure 8:
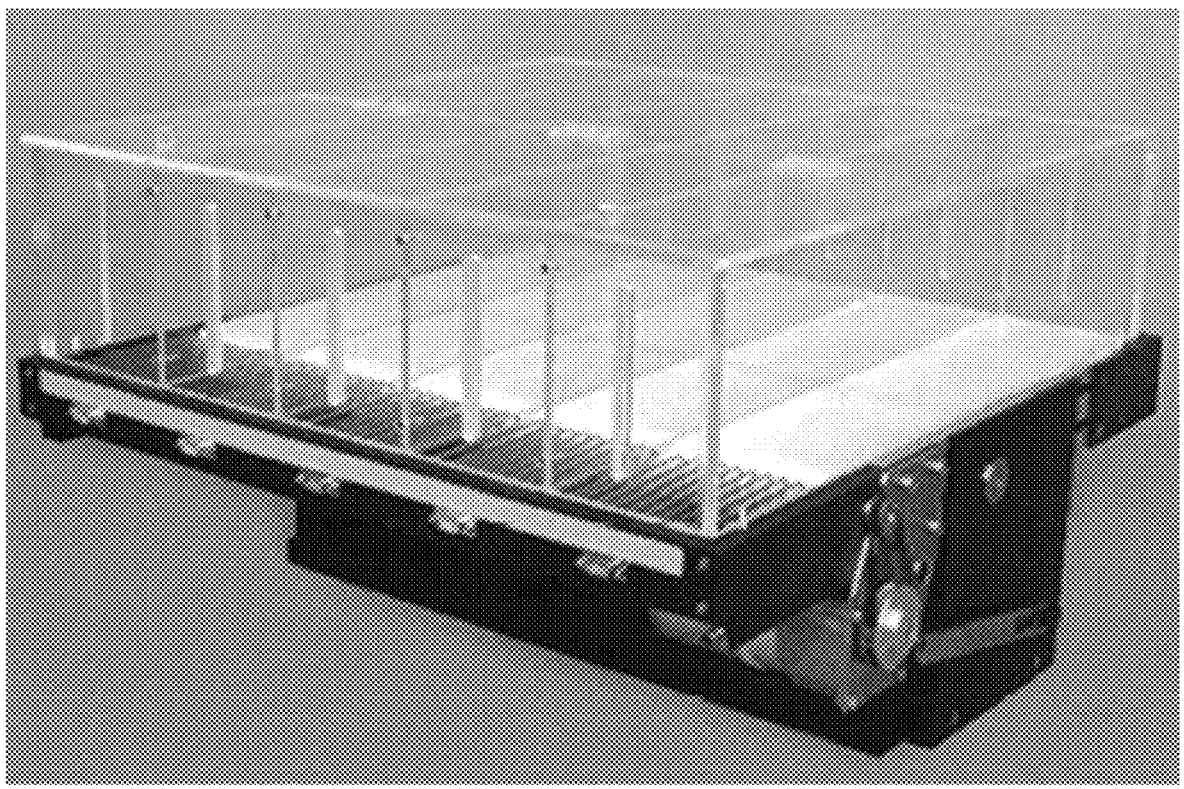
FIG. 8 is a photograph of a device for conducting a treadmill test.

The equipment shown in FIG. 8 was used for the treadmill test.

Figure 9:
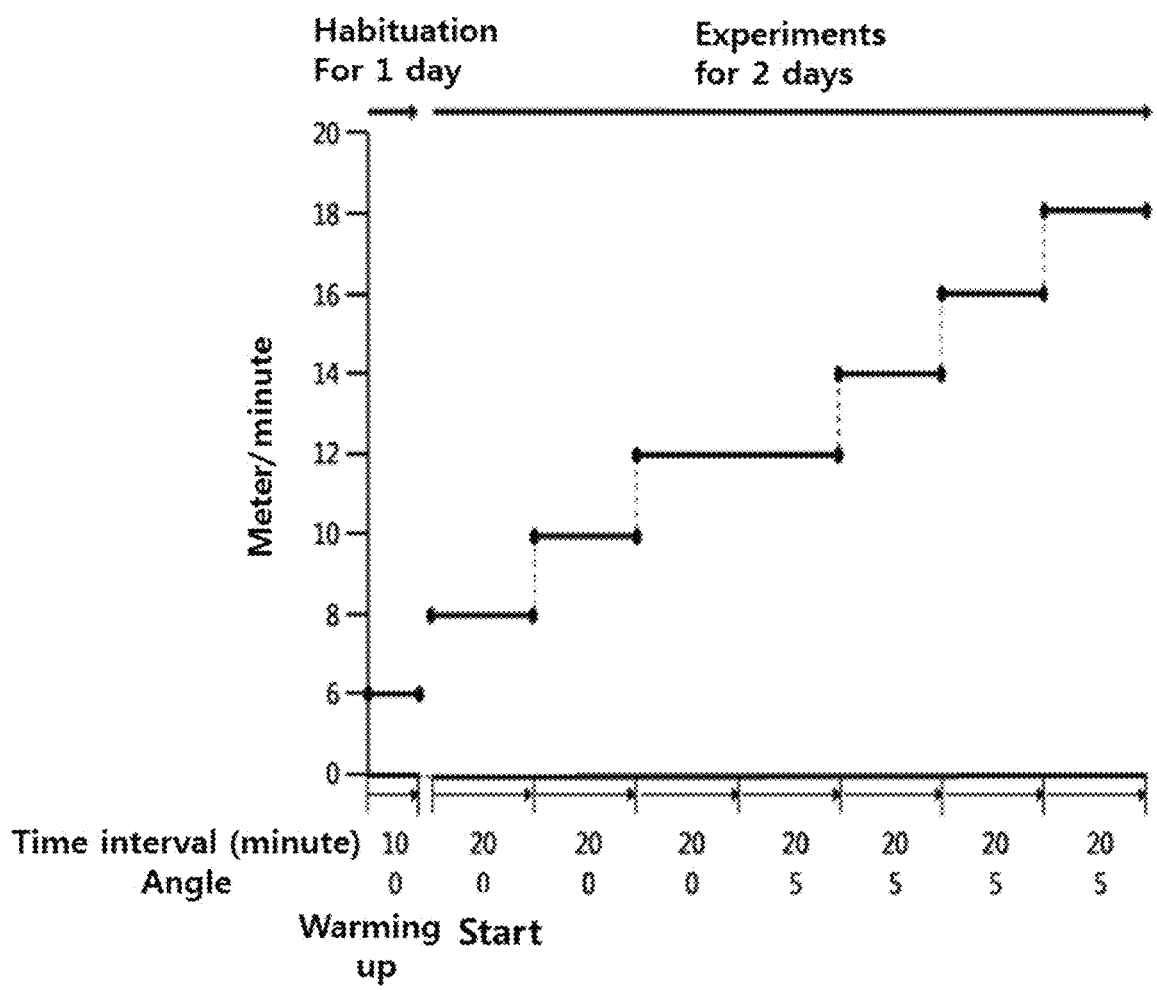
FIG. 9 is a graph showing a process of conducting a treadmill test.

The treadmill test was conducted as shown in FIG. 9 with reference to the treadmill protocol of used for the treadmill test (DOI 10.1016/j.cell.2006.11.013_Cell, Volume 127 Supplemental Data).

One day prior to the treadmill test, the equipment was warmed up at a rate of 6 m/min for 10 minutes. At the starting point, electric stimulation was configured to flow so that the mice were forced to exercise. The next day, the test was started at a speed of 8 m/min and the speed was increased by 2 m/min every 20 minutes. One hour after the the start of the treadmill test, the speed of 12 m/min was maintained, and the angle was increased by 5° and the electric stimulation was turned off. After 20 minutes, the angle of 5° was maintained but only the speed was increased by 2 m/min. Under the above condition, the running times of the mice were measured and recorded.

As a result of the treadmill test, the running time of the negative control group in which distilled water was orally administered was shorter by about 20 minutes or more as compared to the non-immobilization group in which the exercises of the hind limbs were not restricted. In the groups orally administered with sobrerol was, the running time of the mice administered with sobrerol at a concentration of 8.8 mg/kg was slightly longer as compared to the group administered with distilled water, but was still shorter as compared to the non-immobilization group. On the other hand, the running time of the mice administered with sobrerol at a concentration of 17.6 mg/kg was almost similar to the non-immobilization group, and the running time of the mice treated with sobrerol at a dose of 35.3 mg/kg was longer as compared to the non-immobilization group (FIG. 10). These results indicated that sobrerol has the effect of improving muscle strength and promoting recovery of damaged muscles.

Example 3-4: Verification of Effect of Sobrerol on Muscle Size and Muscle Weight In addition, after the exercise restriction in the Example 3-3, sections of the tibialis anterior (TA) were stained by immunofluorescence analysis using the antibodies against laminin, which is a protein existing at the periphery of muscle fibers, and the diameter of each muscle fiber was measured.

Figure 11:
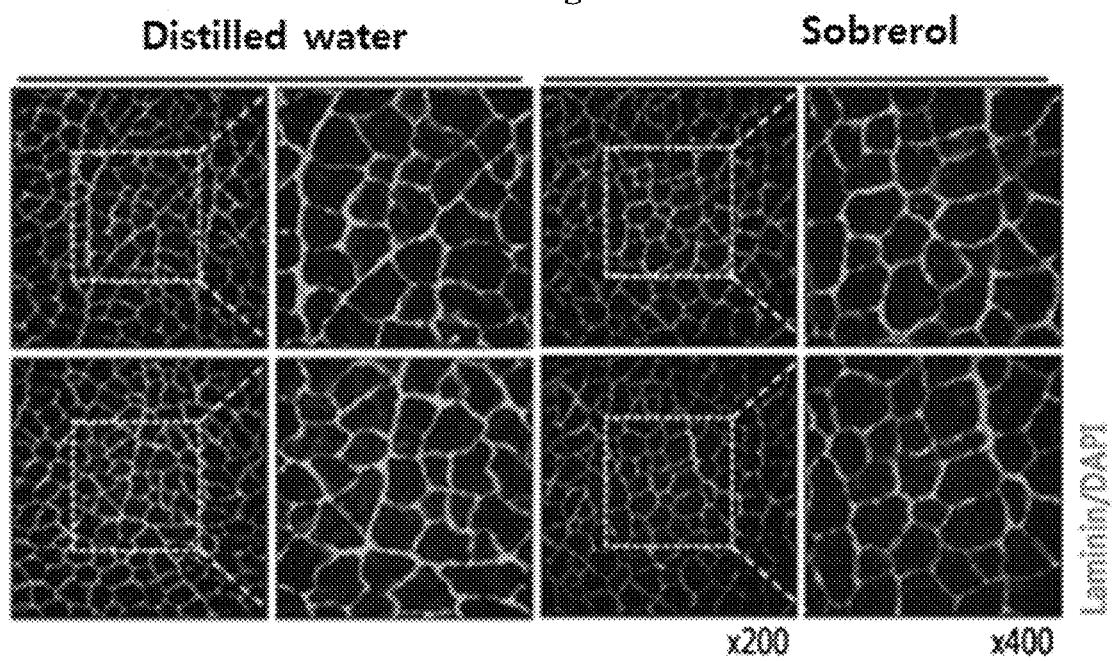
FIG. 11 provides a graph showing changes in muscle size by sobrerol.
Figure 11:
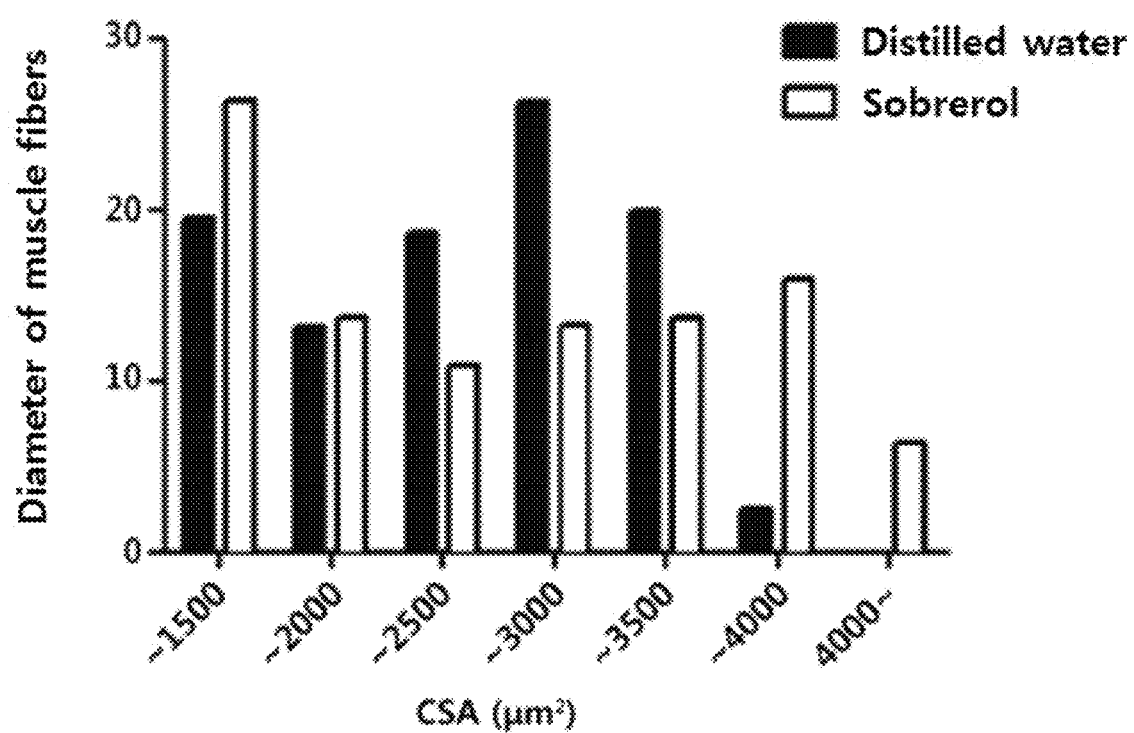
Figure 12:
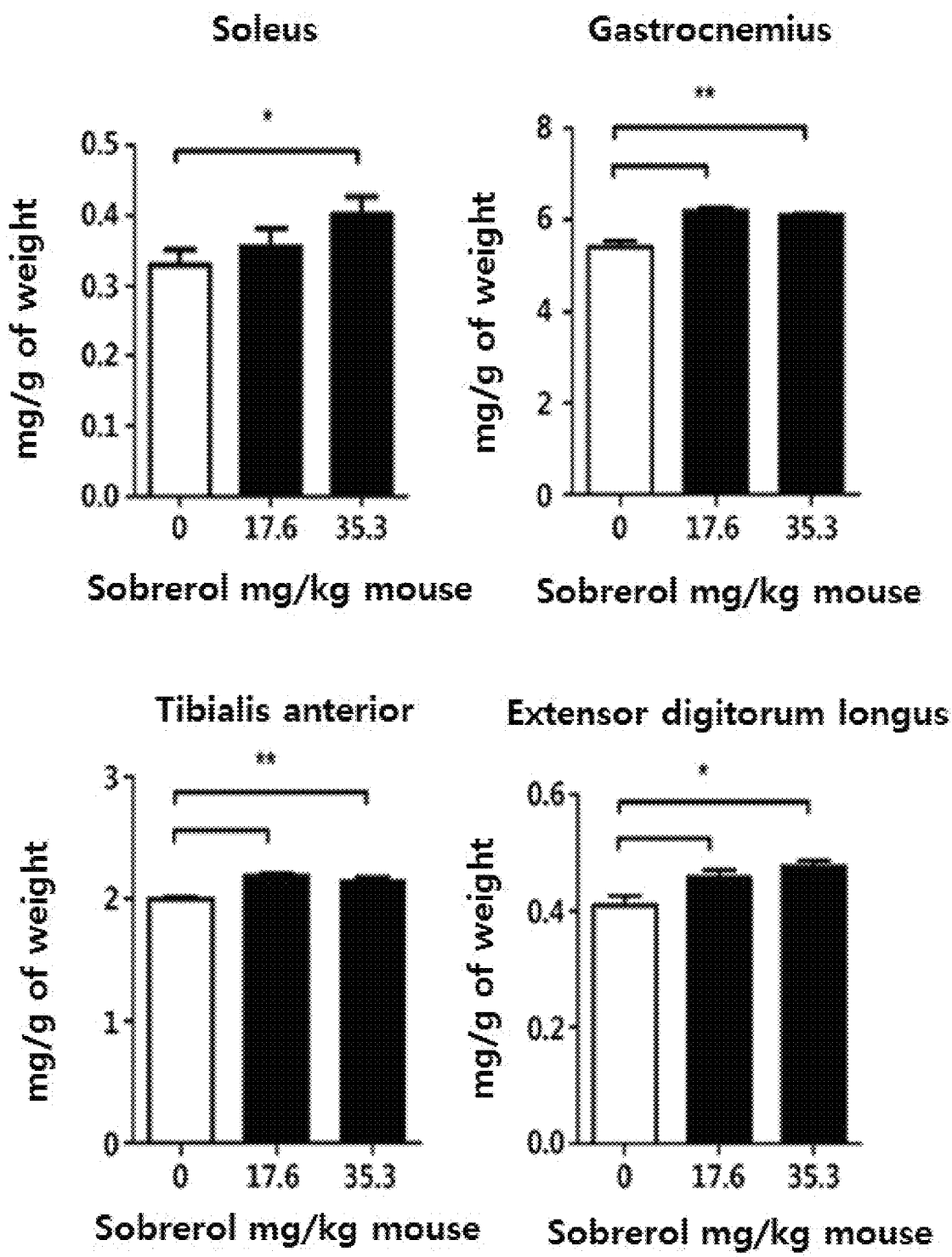
FIG. 12 provides graphs showing changes in muscle weight by sobrerol.

As a result, the diameters of the muscle fibers of the mice orally administered with sobrerol were larger than those of the control group orally administered with distilled water (FIG. 11). In addition, as a result of the muscle weight measurement, the weights of soleus, gastrocnemius (GA), tibialis anterior (TA) and extensor digitorum longus (EDL) were all significantly increased (FIG. 12).

These results indicated that sobrerol has the effect of increasing muscle size and muscle weight.

Example 4: Verification of Effect of Sobrerol on Muscle Strength in Aged Mice

Example 4-1: Experiment Preparation for Verifying Improvement of Exercise Capability of Animals Experiments were conducted to confirm whether sobrerol increases muscle strength in aged mice. Female C57BL/6 mice at the age of 21 months were adapted to the environment for 2 weeks and then orally administered with drugs for 5 weeks. Specifically, the negative control group was administered with water, the positive control group was administered with clenbuterol at a concentration of 2 mg/kg (mouse), and the sobrerol administration experimental group was orally administered with sobrerol at a concentration of 17.6 or 35.3 mg/kg (mouse). Then, locomotion tests (grip strength, treadmill) were conducted again to verify the effect.

Example 4-2: Grip Strength Test

The grip strength test is the same as the Example 3-2.

Figure 13:
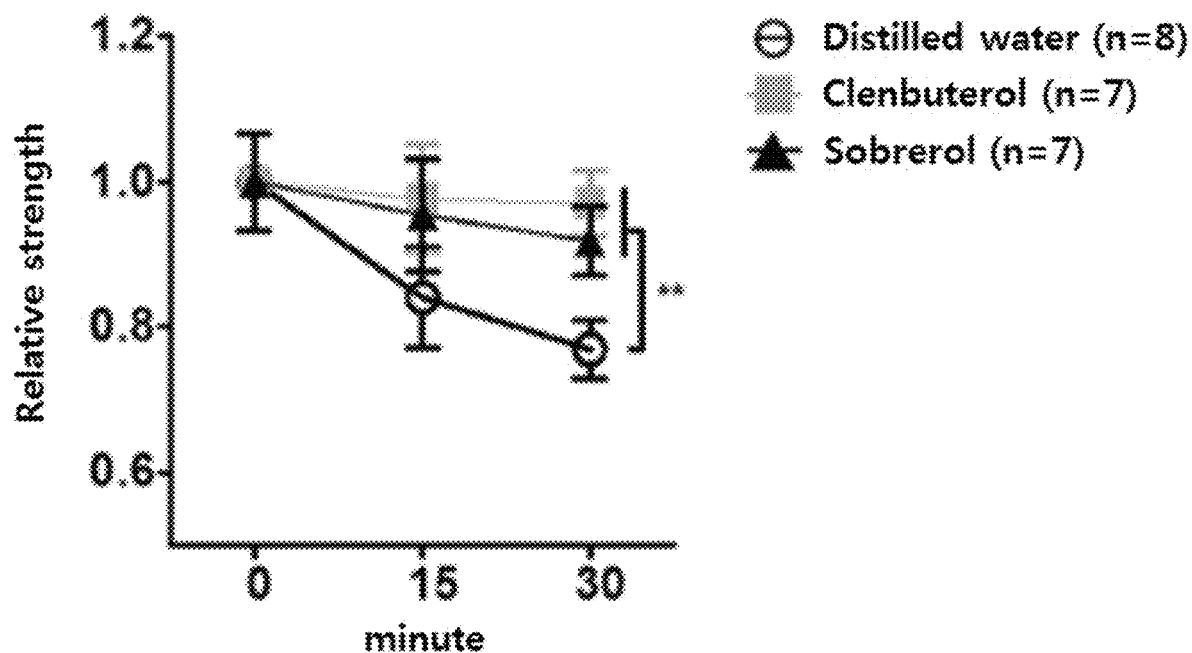
FIG. 13 is a graph showing relative strength as a result of repeated grip strength measurements in aged mice.

As a result, there were no differences in the first measured grip strength values, however when the grip strength was measured repeatedly, the negative control group orally administered with water showed grip strength weakening over time due to the increase in fatigue from exercise. On the other hand, the group orally administered with sobrerol did not show the increase in fatigue similarly to the positive group administered with clenbuterol (FIG. 13).

These results indicated that sobrerol attenuated muscle fatigue in aged mice and had the effect of increasing muscle strength.

Example 4-3: Treadmill Test

Tread mill test is the same as Example 3-3.

Figure 14:
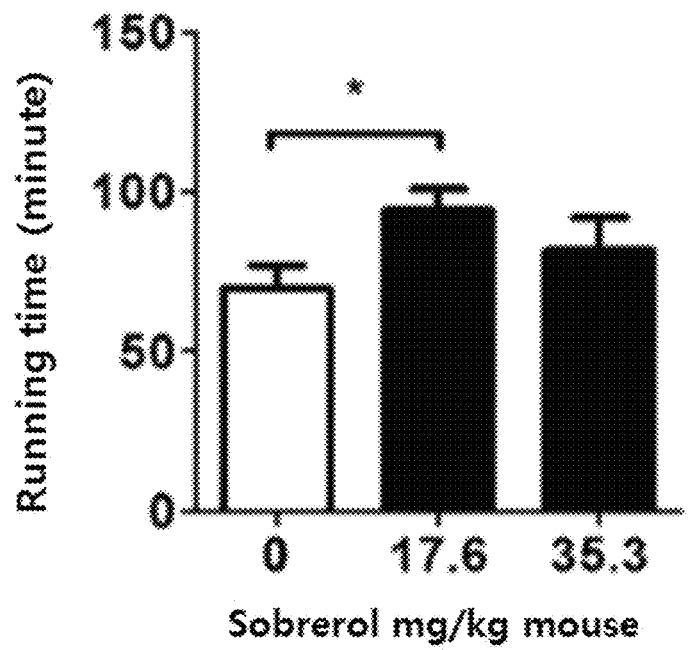
FIG. 14 is a graph showing running times as a result of a treadmill test in the aged mice.

As a result, the experimental group orally administered with sobrerol at a concentration of 17.6 mg/kg (mouse) showed significantly longer running time as compared to the negative control group without sobrerol administration, and the mice administered with sobrerol at a concentration of 35.3 mg/kg also showed longer running time than the negative control group (FIG. 14).

These results indicated that sobrerol has the effect of improving endurance in aged mice.

Example 4-4: Verification of Effect of Sobrerol on Muscle Size and Muscle Weight In addition, changes in the muscle size and the muscle weight of the aged mice by sobrerol were verified by the method of the Example 3-3.

Figure 15:
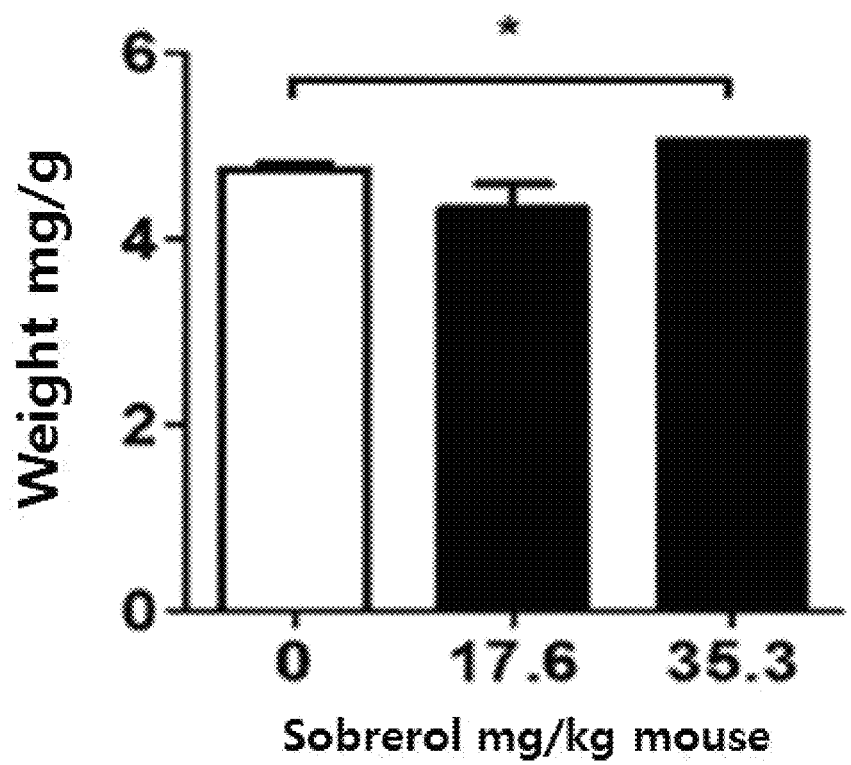
FIG. 15 is a graph showing changes in muscle weight by sobrerol in the aged mice.
Figure 16:
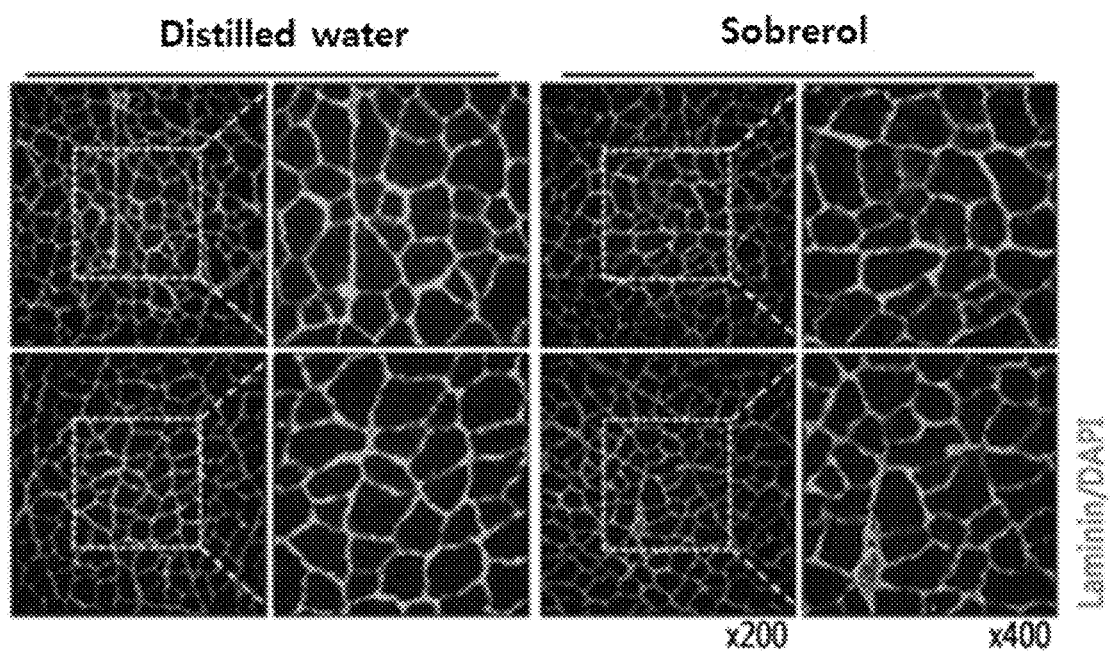
FIG. 16 is a graph showing changes in muscle size caused by sobrerol in the aged mice.
Figure 16:
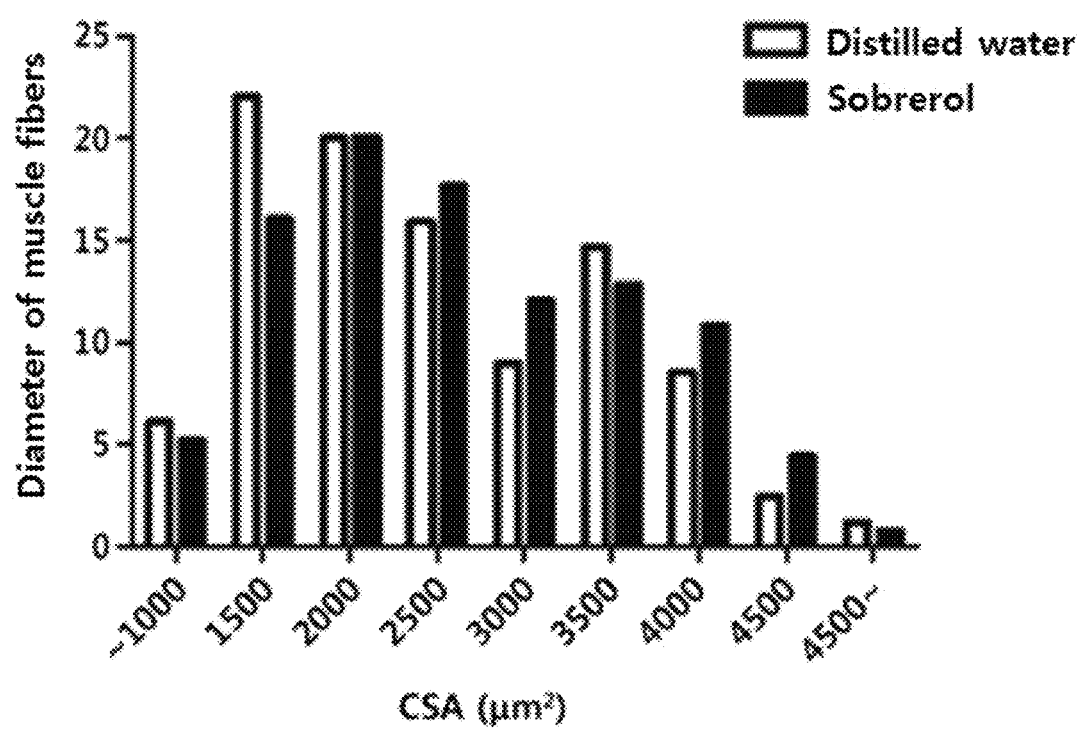

In the Example 4-3, the muscle weights of the experimental group and the negative control group were examined, and as a result, the weights of the gastrocnemius (GA) of the aged mice fed with sobrerol at a concentration of 35.3 mg/kg (mouse) increased to a significant level (FIG. 15). In addition, as in the Example 3-3, the diameter of the muscle fiber of the tibialis anterior (TA) section was measured by immunofluorescence analysis using laminin antibodies. As a result, the diameters of the muscle fibers of the aged mice fed with sobrerol were further increased (FIG. 16).

These results indicated that sobrerol has the effect of increasing muscle size and muscle weight in aged mice.

Example 4-5: Effect of Sobrerol on Muscle Strength in Aged Mice Under Exercise Restriction Conditions In addition, it was examined whether sobrerol increases muscle strength in aged mice after exercise restriction.

Figure 17:
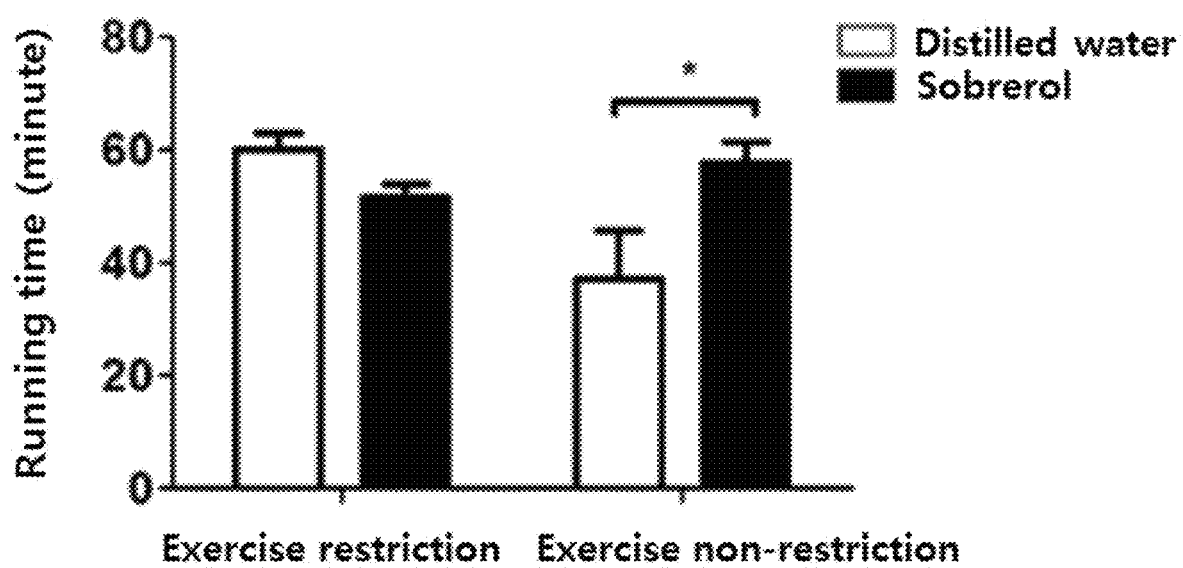
FIG. 17 is a graph showing the running time changed by the sobrerol after exercise restriction of the aged mice.

Both hind limbs of the mice were immobilized for 5 days using a surgical stapler (Autosuture Royal 35W stapler), and after removing the surgical stapler, they were allowed to move again (remobilization), and then exercise capability was evaluated by a treadmill test. As a result, the running time on the treadmill decreased after the exercise restriction as compared to that before the exercise restriction in the control group administered with distilled water, whereas the running time was not affected by exercise restriction in the experiment group administered with sobrerol (FIG. 17).

These results indicated that sobrerol improves the endurance in aged mice under exercise restriction, thereby showing the effect of improving muscle strength.

As can be seen from the above Examples, a composition comprising sobrerol or a pharmaceutically acceptable salt thereof of the present invention has the effect of promoting myogenesis and recovery of damaged muscles in aged mice as well as in model mice, and thus, can be utilized as a composition for promoting differentiation of myoblasts, a pharmaceutical composition for preventing or treating a muscle weakness-related disease, and a composition for increasing muscle strength.

From the above description, it is understood by those skilled in the art that the present invention may be embodied in other forms without departing from the spirit or essential characteristics thereof. In this regard, the above-described embodiments should be understood as illustrative and not restrictive in any respect. The scope of the present invention should be construed as including any modifications or modified forms which can be drawn from the meaning and scope of the appended claims to be described later or any equivalent ideas thereof, rather than being understood based on the above description.

The invention claimed is:

1. A method for treating a subject suffering from muscle weakness-related disease, comprising administering an effective amount of a composition comprising sobrerol or a pharmaceutically acceptable salt thereof to the subject,
   wherein the muscle weakness-related disease is age-related sarcopenia.

2. A method for increasing muscle strength in a subject suffering from a muscle weakness-related disease, comprising administering an effective amount of a composition comprising sobrerol or a pharmaceutically acceptable salt thereof to the subject,
   wherein the muscle weakness-related disease is age-related sarcopenia.

3. The method of claim 1, wherein the composition is selected from the group consisting of a pharmaceutical composition, a health functional food, a feed, and a feed additive.

4. The method of claim 1, wherein a concentration of the sobrerol in the composition ranges from 0.01 nM to 1 µM.

5. The method of claim 2, wherein the composition is selected from the group consisting of a pharmaceutical composition, a health functional food, a feed, and a feed additive.

6. The method of claim 2, wherein a concentration of the sobrerol in the composition ranges from 0.01 nM to 1 µM.

7. The method of claim 1, wherein the administering the composition increases a size of muscle cells in the subject.

8. The method of claim 1, wherein the administering the composition increases a weight of muscle cells in the subject.

9. The method of claim 2, wherein the administering the composition increases a size of muscle cells in the subject.

10. The method of claim 2, wherein the administering the composition increases a weight of muscle cells in the subject.

* * * * *